United States Patent
Nakamura et al.

(10) Patent No.: US 8,288,117 B2
(45) Date of Patent: *Oct. 16, 2012

(54) DRY ANALYTICAL ELEMENT FOR LIPASE MEASUREMENT

(75) Inventors: Kentaro Nakamura, Asaka (JP); Shigeki Kageyama, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 707 days.

This patent is subject to a terminal disclaimer.

(21) Appl. No.: 12/410,046

(22) Filed: Mar. 24, 2009

(65) Prior Publication Data

US 2009/0246812 A1 Oct. 1, 2009

(30) Foreign Application Priority Data

Mar. 25, 2008 (JP) ................................. 2008-077541

(51) Int. Cl.
*C12Q 1/44* (2006.01)
*C12M 1/36* (2006.01)
*C12M 1/34* (2006.01)
*C12M 1/00* (2006.01)

(52) U.S. Cl. .................... 435/19; 435/287.5; 435/287.7; 435/287.9

(58) Field of Classification Search .................... 435/19, 435/287.5, 287.7, 287.9
See application file for complete search history.

(56) References Cited

U.S. PATENT DOCUMENTS

| 4,343,897 A | 8/1982 | Neumann et al. |
| 4,555,483 A | 11/1985 | LiMuti et al. |

FOREIGN PATENT DOCUMENTS

| FR | 2.073.537 A | 10/1971 |
| GB | 1 319 411 A | 6/1973 |
| JP | 59-48098 A | 3/1984 |
| JP | 4-316500 A | 11/1992 |
| JP | 9-154598 A | 6/1997 |
| JP | 2002-125699 A | 5/2002 |

OTHER PUBLICATIONS

Tetrault, "Lipase Activity in Serum Measured with Ektachem is Often Increased in Nonpancreatic Disorders", Clinical Chemistry, vol. 37, No. 3 (1991), p. 447-451.

*Primary Examiner* — Herbert J Lilling

(74) *Attorney, Agent, or Firm* — Birch, Stewart, Kolasch & Birch, LLP

(57) ABSTRACT

It is an object of the present invention to provide: a dry analytical element for analyzing pancreatic lipase wherein the triglyceride is not transcribed on the support to contaminate a transportation slip or other analytical elements and wherein an additive solution of the triglyceride neither reaggregates nor precipitate, so that the dry analytical element is stable and is compatible with production. The present invention provides a dry analytical element for measuring pancreatic lipase contained in body fluid, which comprises triglyceride of long chain alkyl fatty acid having 12 to 22 carbon atoms, monoglyceride lipase, and a glycerin measurement reagent, and which comprises a water-impermeable support and at least one spreading or reagent layer, wherein a hydrophilic polymer at a weight ratio of 1.8:1 or greater with respect to the triglyceride is contained.

17 Claims, 1 Drawing Sheet

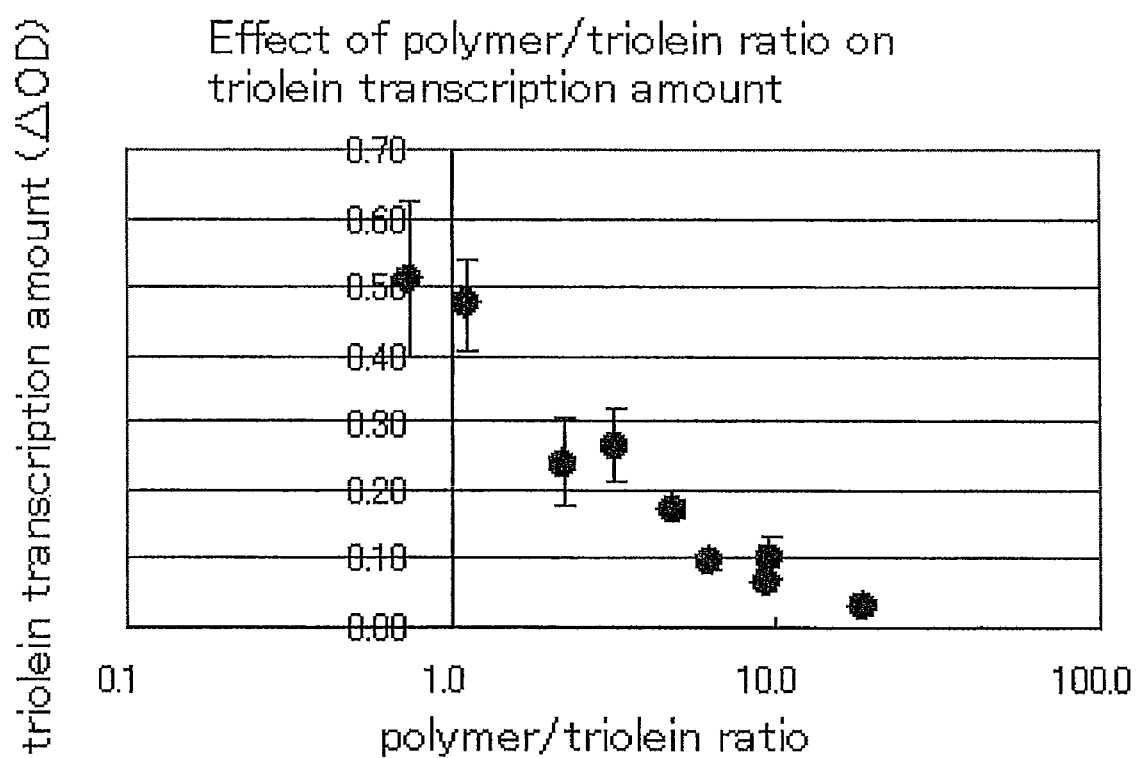

DRY ANALYTICAL ELEMENT FOR LIPASE MEASUREMENT

TECHNICAL FIELD

The present invention relates to: a dry analytical element for measurement of lipase activity, and particularly pancreatic lipase activity, in a liquid sample such as, in particular, the serum or plasma of humans and animals, such analytical element being available for convenient use and having high accuracy; and a method for producing the same. The dry analytical element of the present invention is particularly useful for diagnosing human and canine pancreatic diseases.

BACKGROUND ART

Pancreatic lipase analysis, which is useful for pancreatic disease diagnosis, is often carried out by measuring pancreatic lipase under conditions in which a micellar substrate is dispersed in water in view of the fact that pancreatic lipase functions in oil-water interface. This is because non-pancreatic lipase such as lipoprotein lipase or esterase reacts with a substrate solubilized with a surfactant or the like or with glyceride comprising fatty acid having short alkyl chains. Thus, it is considered that a technically important point for development of dry analytical elements for pancreatic lipase is the incorporation of a long-fatty-acid glyceride serving as a substrate, which is specific to pancreatic lipase, into such analytical element, provided that glyceride is in a state such that it is specific to pancreatic lipase.

Dry analytical elements used for lipase analysis are roughly classified into two types. An example of a first type is a dry analytical element obtained by a method using 1,2-O-dilauryl-rac-glycero-3-glytaric acid/resorufin ester serving as a dye-releasing substrate (JP Patent Publication (Kokai) No. 9-154598 A (1997)). Such method is preferable because high specificity with respect to pancreatic lipase can be achieved and a glycerin coloring system is unnecessary. However, such substrate incorporated into a dry analytical element is highly likely to disintegrate. Thus, such dry analytical element has still not been available in practice, although it has been attempted to separate a low-pH layer containing a lipase substrate from another high-pH reagent layer. In addition, the relatively high price of such a substrate is also problematic in terms of practical use.

An example of a second type is a dry analytical element for lipase analysis, in which a method for converting triglyceride used as a substrate into a dye via glycerin and hydrogen peroxide is used. According to the first disclosed method, it is a multilayer dry analytical element (JP Patent Publication (Kokai) No. 59-48098 A (1984)), wherein triglyceride having a long chain alkyl group having at least 8 carbon atoms at an ester position (α position) and two other esters each having a short chain alkyl group is used as a substrate, water-soluble 1,2 diacetylglyceride generated in the presence of lipase in a specimen is converted into glycerin with the use of an esterase (namely, acetinase), and glycerin is converted into a dye. The above method is a convenient and highly accurate lipase measurement method. However, it has been reported that selectivity with respect to pancreatic lipase is not high, and thus that attention is required if this method is applied to the diagnosis of pancreatic diseases [Clin. Chem., 37/3, 447-451 (1991)]. Such problem regarding specificity may be caused by the fact that triglyceride used as a substrate also contains a short chain alkyl group.

Next, there has been disclosed a method, which also uses triglyceride as a substrate. That is, there has been disclosed a dry chemistry reagent for pancreatic lipase analysis, which comprises triglyceride having only a long chain fatty acid containing 14 to 20 carbon atoms, such as triolein, as a substrate and which further comprises monoglyceride lipase and a glycerin measurement reagent (JP Patent Publication (Kokai) No. 4-316500 A (1992)). Such a method using triolein is anticipated to be highly specific to pancreatic lipase. However, in this triolein addition method, since a highly fat-soluble substrate is incorporated, a protective colloid such as gum Arabic is used to carry out aqueous emulsification dispersion involving an ultrasonic treatment (JP Patent Publication (Kokai) No. 4-316500 A (1992): Examples). In this emulsification dispersion method, it is necessary to maintain the reproducibility of substrate dispersion and uniformity in particle size distribution. Thus, it is thought that production by such method is difficult.

For instance, JP Patent Publication Kokai) No. 4-316500 A (1992) contains the following description: "triglyceride, such as triolein, comprising a long chain fatty acid in each of three ester positions has the property of being emulsified with difficulty. Thus, even if a solution in which triolein has been uniformly emulsified and dispersed via agitation or by physical shearing force generated by ultrasound waves or the like is added in the presence of a surfactant or a protective colloid upon preparation of a dry reagent, water serving as a dispersion medium disappears when the reagent becomes dry, and thus an emulsified product aggregates or coalesces so as to adhere to the surface of a spreading layer, resulting in significant reduction in the surface area in oil-water interface. Upon measurement, even if a specimen (liquid) containing lipase is allowed to react with such dry reagent, triolein remains in a state of aggregating or coalescing and thus does not return to the original state of being dispersed because of lack of physical shearing force. The reaction field of lipase is an oil-water interface. Thus, a decrease in the surface area of an oil-water interface is thought to cause a decrease in reaction rate."

In addition, in the examples of the method of JP Patent Publication (Kokai) No. 4-316500 A (1992), a filter and a nylon film is impregnated with a reagent. However, since a support is not used to maintain strength in the examples, it is considered difficult to carry out transportation and winding at a constant rate/high rate in the production process. Thus, in order to produce a dry analytical element having both measurement accuracy and productivity, addition of a support is almost essential.

A method modified from the method of JP Patent Publication (Kokai) No. 4-316500 A (1992), which comprises adding a support to produce a multilayer analytical element with high accuracy and incorporating fine particles therein so as to enhance lipase reactivity is described in JP Patent Publication (Kokai) No. 2002-125699 A. The applicant has further modified this method. The applicant has conceived of a method of adding glyceride, such as triolein, dissolved in an organic solvent such as ethanol to an analytical element comprising a support, thereby producing a dry analytical element that is highly specific to pancreatic lipase.

However, when such a dry analytical element comprising a support necessary for stable production and using triolein as a substrate was produced, unexpectedly, another serious problem occurred. That is to say, the following was found. That is, since triolein is oil, such triolein added to the reaction layer of lipase is easily transcribed on the back side of the support when the transported product is wound, and the transcribed triolein on the support is then transcribed on a pass roll used in transportation. The thus transcribed triolein reduces a friction between the pass roll necessary for transportation and the support, and transportation slip is thereby generated. In order to produce highly accurate dry analytical element, it is necessary to add a constant amount of reagent by coating, impregnation, etc. Generation of a slip during transportation makes addition of a constant amount of reagent impossible. This makes production of a dry analytical element for lipase measurement impossible. At the same time, it means that a producing apparatus having a transportation system, which has become contaminated by oil, cannot be used to produce products (e.g. a glucose analyzing device, a cholesterol analyzing device, etc.) used in highly accurate clinical analyses that require addition of a constant amount of reagent. Moreover, triolein transcribed on the support not only causes malfunction to the transportation system, but it also gives a positive error when it is transcribed on a device for measuring and analyzing neutral fats.

Due to the aforementioned problems, the product disclosed in JP Patent Publication (Kokai) No. 59-48098 A (1984) is still the only commercially available dry analytical element for lipase analysis, although the product has low pancreatic lipase specificity. Thus, dry analytical elements that are excellent in terms of reliability for diagnosis of pancreatic diseases have been awaited in the market.

DISCLOSURE OF THE INVENTION

It is an object of the present invention to provide: a dry analytical element for analyzing pancreatic lipase, which uses long chain fatty acid triglyceride such as triolein as a substrate and which comprises a support, wherein the triglyceride is not transcribed on the support to contaminate a transportation slip or other analytical elements and wherein an additive solution of the triglyceride neither reaggregates nor precipitate, so that the dry analytical element is stable and is compatible with production; and a method for producing the same.

In view of the above circumstances, the present inventors conducted intensive studies. As a result, they have found that transcription of triglyceride on a support can be reduced, and a transportation slip can be reduced or eliminated in the production process, and a contamination of triglyceride to analytical slide can be prevented, by applying a structure of a dry multilayer analytical element, which comprises long chain fatty acid triglyceride highly specific to pancreatic lipase, and also comprises monoglyceride lipase and a glycerin coloring system for color development, and further comprises a support that can realize convenient and highly accurate analysis, wherein the dry multilayer analytical element comprises a hydrophilic polymer at a weight ratio of 1.8:1 or greater with respect to the triglyceride, thereby completing the present invention.

The present invention provides a dry analytical element for measuring pancreatic lipase contained in body fluid, which comprises triglyceride of long chain alkyl fatty acid having 12 to 22 carbon atoms, monoglyceride lipase, and a glycerin measurement reagent, and which comprises a water-impermeable support and at least one development or reagent layer, wherein a hydrophilic polymer at a weight ratio of 1.8:1 or greater with respect to the triglyceride is contained.

Preferably, a hydrophilic polymer at a weight ratio of 5:1 or greater with respect to the triglyceride is contained.

Preferably, a hydrophilic polymer at a weight ratio of 10:1 or greater with respect to the triglyceride is contained.

Preferably, the hydrophilic polymer is selected from among polyvinylpyrrolidone, polyacrylamide, a cellulose derivative, gelatin, and a combination thereof.

Preferably, the cellulose derivative is hydroxypropylcellulose, hydroxyethylcellulose, or methylcellulose.

Preferably, the glycerin measurement reagent comprises glycerin kinase, glycerophosphate kinase, peroxidase, and a coloring reagent.

Preferably, the monoglyceride lipase is derived from *Bacillus stearothermophilus* H-165.

Preferably, the triglyceride is triolein.

Preferably, the dry analytical element for measuring pancreatic lipase contained in body fluid has a structure comprising a water-impermeable support, a reagent layer, and a spreading layer.

Preferably, the spreading layer consists of a fabric or a porous membrane.

Preferably, the porous membrane is a porous membrane of acetylcellulose or polysulfone, or a porous membrane formed from microbeads.

The present invention further provides a method for producing a dry analytical element for measuring pancreatic lipase contained in body fluid, which comprises triglyceride of long chain alkyl fatty acid having 12 to 22 carbon atoms, monoglyceride lipase, and a glycerin measurement reagent, and which comprises a water-impermeable support and at least one spreading or reagent layer, which comprises a step of coating the triglyceride in a state where the dry analytical element comprises a hydrophilic polymer at a weight ratio of 1.8:1 or greater with respect to the triglyceride.

Preferably, the triglyceride is coated in a state where the dry analytical element comprises a hydrophilic polymer at a weight ratio of 5:1 or greater with respect to the triglyceride.

Preferably, the triglyceride is coated to the dry analytical element in a state where the dry analytical element comprises a hydrophilic polymer at a weight ratio of 10:1 or greater with respect to the triglyceride.

Preferably, the hydrophilic polymer is selected from among polyvinylpyrrolidone, polyacrylamide, a cellulose derivative, gelatin, and a combination thereof.

Preferably, the cellulose derivative is hydroxypropylcellulose, hydroxyethylcellulose, or methylcellulose.

Preferably, the triglyceride is triolein.

A dry analytical element for measuring pancreatic lipase contained in body fluid was produced, which comprises triglyceride of long chain fatty acid having 12 to 22 carbon atoms, monoglyceride lipase, and a glycerin measurement reagent, and which comprises a water-impermeable support and at least one spreading or reagent layer. As a result, a dry analytical element having good basic performance could be produced, but upon transportation during the production process, the support was slipped, and thus it became impossible to conduct transportation at a constant rate. This is because a friction of the support was reduced due to a slight transcription of the triglyceride on the support. In the present invention, the amount of triglyceride transcribed on the support could be reduced by adding a hydrophilic polymer to the dry analytical element at a weight ratio of 1.8:1 or greater with respect to the triglyceride, and the aforementioned problem regarding slip could be solved thereby. Moreover, a Fuji Dry Chem (FDC) neutral fat measurement and detection element for measuring triglyceride (neutral fat) could be prevented from contamination. Herein, it is considered that a mechanism of suppressing transcription of triglyceride using a hydrophilic polymer could be brought on by covering triglyceride oil droplets added into a spreading layer with the hydrophilic polymer, thereby preventing the movement (transcription) of the oil droplets.

BRIEF DESCRIPTION OF THE DRAWING

FIG. 1 shows the influence of the polymer/triolein ratio upon the amount of triolein transcribed.

BEST MODE FOR CARRYING OUT THE INVENTION

Hereinafter, the present invention will be described more in detail.

The dry analytical element for measuring pancreatic lipase contained in body fluid according to the present invention, which comprises triglyceride of long chain alkyl fatty acid having 12 to 22 carbon atoms, monoglyceride lipase, and a glycerin measurement reagent, and which comprises a water-impermeable support and at least one spreading or reagent layer, is characterized in that a hydrophilic polymer at a weight ratio of 1.8:1 or greater with respect to the triglyceride is contained.

Hydrophilic Polymer Used in the Present Invention

Examples of a hydrophilic polymer used in the present invention include starch, cellulose, cellulose derivatives (e.g., methylcellulose, hydroxyethylcellulose, and hydroxypropylcellulose), agarose, gelatins (e.g., an acid-treated gelatin and a deionized gelatin), gelatin derivatives (e.g., a phthalated gelatin and a hydroxyacrylate graft gelatin), acrylamide polymers, copolymers each comprising acrylamide and a different vinyl monomer, vinylpyrrolidone polymers, copolymers each comprising vinylpyrrolidone and a different vinyl monomer, acrylate polymers, and copolymers each comprising acrylate and a different vinyl monomer. Particularly preferred examples of such a hydrophilic polymer include polyvinylpyrrolidone, polyacrylamide, cellulose derivatives, and gelatin.

Preferably, such cellulose derivatives are selected from among hydroxypropylcellulose, hydroxyethylcellulose, and methylcellulose. More preferably, such hydrophilic polymers include hydroxypropylcellulose and gelatin.

The hydrophilic polymer is used at a weight ratio of 1.8:1 or greater, preferably 5:1 or greater, and more preferably 10:1 or more, with respect to triglyceride.

<Triglyceride>

In order to improve specificity to pancreatic lipase, the triglyceride used in the present invention is a triglyceride of long chain alkyl chain fatty acid. The long chain alkyl chain may be saturated or unsaturated. An unsaturated fatty acid triglyceride is preferable. The reactivity of unsaturated fatty acid with pancreatic lipase is relatively low. In terms of selectivity for pancreatic lipase, the alkyl chain length of the long chain alkyl chain fatty acid may be 12 to 22 carbon atoms, and it may be preferably 16 to 20 carbon atoms. Several examples will be given below.

Examples of saturated fatty acids include lauric acid ($C_{12:0}$), myristic acid ($C_{14:0}$), palmitic acid ($C_{16:0}$), stearic acid ($C_{18:0}$), arachic acid ($C_{20:0}$), and behenic acid ($C_{22:0}$). Examples of unsaturated fatty acids include palmitoleic acid ($C_{16:1}$), petroselinic acid ($C_{11}H_{23}COOH$), oleic acid ($C_{18:1}$), linolic acid ($C_{18:1}$), linolenic acid ($C_{18:2}$), eleostearic acid ($C_{18:3}$), and arachidonic acid ($C_{20:4}$). Among them, unsaturated fatty acid triglyceride is preferable. Triglycerides of oleic acid and linolic acid are preferable. A particularly preferred triglyceride is triolein, which is a triglyceride of oleic acid.

<Monoglyceride Lipase>

Monoglyceride lipase is added to a reagent system that is incorporated into the dry analytical element of the present invention. A preferred example of monoglyceride lipase is one that does not substantially react with triglyceride and diglyceride but reacts with monoglyceride of long chain fatty acid. *Bacillus stearothermophilus* H-165-derived monoglyceride lipase described in JP Patent Publication (Kokai) No. 63-245672 A (1988) and JP Patent Publication (Kokai) No. 4-316500 A (1992) is particularly preferable.

<Glycerin Measurement Reagent>

In the measurement reaction system used in the present invention, monoglyceride generated by degradation of triglyceride used as a substrate with lipase as a measurement target is decomposed with monoglyceride lipase. In a preferred glycerin coloring system, L-α-glycerophosphate is obtained from the resulting glycerol with the use of glycerol kinase. Then, L-α-glycerophosphate is turned into dihydroxyacetone phosphate with L-α-glycerophosphate oxidase, and hydrogen peroxide is generated. Coloring from a coloring dye is induced by the function of peroxidase with the use of hydrogen peroxide.

Glycerol kinase allows glycerol and ATP to react with each other so as to change them into L-α-glycerophosphate(L-glycerol-3-phosphate) and ADP, respectively. It uses coenzymes such as $Mg^{2+}$ and $Me^{2+}$.

L-α-glycerophosphate oxidase(glycerol-3-phosphate oxidase)oxidizes L-glycerophosphate so as to change it into dihydroxyacetone phosphate and generate hydrogen peroxide.

Various coloring systems in which coloring is caused by the function of peroxidase with the use of hydrogen peroxide have been developed for dry analytical elements. Thus, it is possible to appropriately select and use one thereof. Most of them are leuco dyes represented by o-toluidine.

<Layer Structure>

As a layer structure, the dry analytical element of the present invention comprises at least one spreading layer or reagent layer, and a support which is used to further enhance measurement accuracy and strength and to improve transporting ability during a production process. In the simplest form, the layer consists of support and a spreading layer having the functions as a reagent layer. The number of such layers may be increased.

<Support>

A light-permeable and water-impermeable support can be used to constitute a support layer of the dry analytical element for lipase measurement of the present invention. When measurement is conducted from the spreading layer side, a light-impermeable support may be used. The support gives strength to the dry analytical element and improves the production efficiency. An example of a light-permeable/water-impermeable support is a film- or sheet-type transparent support having a thickness of approximately 50 μm to 1 mm and preferably approximately 80 μm to 300 μm and comprising polymers such as polyethylene terephthalate, polycarbonate of bisphenol A, polystyrene, cellulose ester (e.g., cellulose diacetate, cellulose triacetate, or cellulose acetate propionate). In terms of strength and optical properties, a preferred material is polyethylene terephthalate.

An undercoat layer is provided on the surface of a support, as necessary, such that adhesion between a reaction layer provided on the support and the support can be strengthened. In addition, physical or chemical activation treatment is carried out on the support surface, instead of provision of an undercoat layer, such that adhesivity can be improved.

<Reagent Layer>

A reagent layer may be provided on a support (via another layer such as an undercoat layer in some cases). A reagent layer is a water-absorbing and water-permeable layer containing a hydrophilic polymer binder in which at least a portion of a reagent composition described below, such composition reacting with lipase serving as an analyte so as to cause optically detectable changes, is substantially uniformly dispersed.

A hydrophilic polymer that can be used as a binder for a reaction layer is generally a natural or synthetic hydrophilic polymer having a swelling rate upon water absorption at 30° C. in the range of approximately 150% to 2000% and preferably of approximately 250% to 1500%. Examples of such hydrophilic polymer include gelatins (e.g., acid-treated gelatin and deionized gelatin), gelatin derivatives (e.g., phthalated gelatin and hydroxyacrylate graft gelatin), agarose, pullulan, pullulan derivatives, polyacrylamide, polyvinyl alcohol, and polyvinylpyrrolidone, which are disclosed in JP Patent Publication (Kokai) No. 58-171864 A (1983), JP Patent Publication (Kokai) No. 60-108753 A (1985), and the like.

A reagent layer may be a layer that has been appropriately cross-linked and cured using a crosslinking agent. Examples of a crosslinking agent include: conventional vinyl sulfone crosslinking agents such as 1,2-bis(vinyl sulfonylacetamide) ethane and bis(vinyl sulfonylmethyl)ether; aldehyde and the like for gelatin; and aldehyde and epoxy compounds comprising two glycidyl groups and the like for a methallyl alcohol copolymer.

The thickness of a reagent layer when dried is preferably in the range of approximately 1 μm to 100 μm and more preferably of approximately 3 μm to 30 μm. Preferably, a reagent layer is substantially transparent.

<Spreading Layer>

According to the present invention, it is preferable to use a fabric spreading layer as a porous spreading layer. Alternatively, it is also possible to use a non-fabric material such as a porous membrane of polysulfone or acetylcellulose, porous membrane formed with microbeads, glass fiber filter paper, or filter paper.

<Fabric>

Examples of the porous spreading layer of fabric include woven fabric spreading layers (e.g., plain weave fabric such as broadcloth or poplin) described in JP Patent Publication (Kokai) No. 55-164356 A (1980), JP Patent Publication (Kokai) No. 57-66359 A (1982), and the like; knitted fabric spreading layers (e.g., tricot knitted fabric, double tricot knitted fabric, and Milanese knitted fabric) described in JP Patent Publication (Kokai) No. 60-222769 A (1985) and the like; and a spreading layer comprising woven fabric or knitted fabric subjected to etching treatment with an alkaline etching solution described in JP Patent Publication (Kokai) No. 1-172753 A (1989). Knitted fabric is preferable. In particular, tricot knitted fabric is preferable. Examples of fabric material used include polyester, cotton, nylon, silk, vinylon, rayon, polyamide, acrylic, wool, polypropylene, and hemp. Preferably, polyester is used. The appropriate thickness of the spreading layer is approximately 50 to 400 μm and preferably approximately 200 to 400 μm. The porosity of fabric is approximately 20% to 90% and preferably approximately 40% to 85%.

In the cases of woven fabric and knitted fabric used for a porous spreading layer, it is possible to improve the adhesivity of such fabric to a lower layer (close to a support) by carrying out a physical activation treatment represented by a glow discharge treatment or corona discharge treatment disclosed in JP Patent Publication (Kokai) No. 57-66359 A (1982) on at least one side of the fabric or by hydrophilizing the fabric in a manner such that a washing and degreasing treatment and/or a hydrophilization treatment involving surfactant impregnation, hydrophilic polymer impregnation, or the like, which are disclosed in JP Patent Publication (Kokai) No. 55-164356 A (1980), JP Patent Publication (Kokai) No. 57-66359 A (1982) and the like, are carried out, or such that a treatment involving an appropriate combination of the above treatments is carried out in a sequential manner.

When a porous layer is used as a spreading reaction layer, a porous medium thereof may be fibrous or nonfibrous. Examples of a fibrous material that can be used include filter paper, nonwoven fabric, woven fabric (e.g., plain weave fabric), knitted fabric (e.g., tricot knitted fabric), and glass fiber filter paper. Examples of a nonfibrous material include a membrane filter comprising cellulose acetate and the like disclosed in JP Patent Publication (Kokai) No. 49-53888 A (1974), and a particulate unit layer having continuous voids, such layer comprising fine particles of an inorganic or organic substance disclosed in JP Patent Publication (Kokai) No. 49-53888 A (1974), JP Patent Publication (Kokai) No. 55-90859 A (1980) (corresponding to U.S. Pat. No. 4,258,001), JP Patent Publication (Kokai) No. 58-70163 A (1983) (corresponding to U.S. Pat. No. 4,486,537), and the like.

Also, layer laminated products having a plurality of porous layers that partially adhere to each other disclosed in the following documents and the like are preferable: JP Patent Publication (Kokai) No. 61-4959 A (1986) (corresponding to EP 0166365 A); JP Patent Publication (Kokai) No. 62-116258 A (1987); JP Patent Publication (Kokai) No. 62-138756 A (1987) (corresponding to EP 0226465 A); JP Patent Publication (Kokai) No. 62-138757 A (1987) (corresponding to EP 0226465 A); and JP Patent Publication (Kokai) No. 62-138758 A (1987) (corresponding to EP 0226465 A).

In order to add a reagent to a spreading layer, a spreading layer is first formed and then a reaction reagent may be added by means of coating or the like. Alternatively, an example of a useful method is the method comprising impregnating a porous membrane or the like composed of paper, fabric, a polymer, or the like with the reagent of the present invention or coating the reagent thereto and allowing the resultant to adhere to another water-permeable layer formed on a support as described in JP Patent Publication (Kokai) No. 55-164356 A (1980).

A porous layer may be a spreading layer having a so-called measuring function that allows a supplied liquid to be developed in an area that is almost in proportion to the amount of the liquid. It is effective to control such function with the use of a surfactant and a hydrophilic binder.

It is also possible to provide a layer that differs from the above layers to the dry analytical element of the present invention. Examples thereof include a light-shielding layer, a water-absorbing layer, and an adhesive layer.

In order to increase the reactivity of pancreatic lipase mainly contained in blood that serves as a measurement target of the present invention, as a reagent to be incorporated into the dry analytical element of the present invention, collapse is preferably added to the reagent system of the present invention. A preferred example of such collapse is pig-pancreas-derived colipase. In addition, in order to increase the activity of pancreatic lipase and to reduce the lipase activity of non-pancreatic lipase, deoxycholic acid or taurocholic acid is added as an activating agent. Thus, influences of esterase, liver lipase, and lipoprotein lipase are removed, and thus pancreatic lipase can be measured with high specificity.

The contents of the above reagents are as follows: triglyceride: approximately 0.1 to 15 $g/m^2$ and preferably approximately 0.5 to 10 $g/m^2$; glycerol kinase: 0.5 to 100 $KU/m^2$ and preferably approximately 1 to 10 $KU/m^2$; L-α-glycerophosphate oxidase: approximately 2 to 200 $KU/m^2$ and preferably approximately 1 to 30 $KU/m^2$; peroxidase: approximately 1 to 200 $KU/m^2$ and preferably approximately 1 to 50 $KU/m^2$; monoglyceride lipase: approximately 2 to 100 $KU/m^2$ and preferably approximately 3 to 30 $KU/m^2$; a coloring dye: approximately 0.05 to 2.00 $g/m^2$ and preferably approximately 0.1 to 1.00 $g/m^2$; colipase: preferably 0.010 to 0.400 $g/m^2$; deoxycholic acid: approximately 0.1 to 10 $g/m^2$; taurodeoxycholic acid: approximately 0.05 to 10 $g/m^2$.

Monoglyceride lipase used herein is in an amount of preferably 8000 $U/m^2$ to 1000 $U/m^2$, more preferably 5000 $U/m^2$ to 2000 $U/m^2$. Although monoglyceride lipase is a conjugated enzyme, it is not preferable to add it in an excessive amount. When diglyceride is used as a substrate, the background level might be increased. In addition, even when triglyceride is used as a substrate, the reaction of a part of lipoprotein in blood is induced along with increases in the amount of monoglyceride lipase, resulting in the generation of measurement errors.

All of the reagent composition may be contained in a reaction layer or spreading layer. Alternatively, it may be divided such that it is contained in both layers, or it may be partially contained in another layer.

It is also possible to add other reagents, such as a buffer and a surfactant, to the dry analytical element of the present invention.

Examples of a buffer that can be contained in the dry analytical element of the present invention include known buffers such as a carbonate buffer, a borate buffer, a phosphate buffer, a tris salt buffer, and a Good's buffer. These buffers can be selected and used by referring to known references such as "Primary Experimental Methods for Proteins and Enzymes (*Tanpakushitsu/Koso no Kiso Jikken-hou*)" (Takeichi Kajio et al, Nankodo Co., Ltd., 1981). The content thereof may be approximately equal to that generally used in an integrated multilayer analytical element, which is in the range of approximately 100 $mg/m^2$ to 20 $g/m^2$ and preferably of approximately 1 $g/m^2$ to 10 $g/m^2$.

In the case of analysis using a dry analytical element, the analysis is carried out without diluting a specimen. Thus, the analysis is easily affected by various ingredients contained in the specimen. In order to solve such problem regarding a difference in such lipase activation among specimens, addition of alkylphenylsulfonate such as sodium dodecylbenzenesulfonate was found to be useful. That is to say, in analyses using the conventional dry analytical elements, poor multi-specimen correlation was provided due to poor lipase reactions of several specimens. In order to solve this problem, alkylphenylsulfonate such as sodium dodecylbenzenesulfonate was added to a dry analytical element, so as to succeed in significantly improving a correlation coefficient. This result was obtained because the lipase activity of specimens having negative errors in the correlation was recovered.

Examples of an anionic surfactant used in the present invention include those having a carboxyl group, a sulfonic acid group, a sulfate group or a phosphate as a hydrophilic group. Preferred anionic surfactants having a sulfonic acid group that can be used in the present invention include alkylbenzenesulfonate, alkylnaphthalenesulfonate, akylsulfate, a polyoxyethylene alkyl ether sulfate, α-olefin sulfonate, and N-acylmethyl taurine salts. The number of carbon atoms of a hydrophobic group is preferably approximately 12 to 20. Among others, those that do not inhibit lipase activity and do not deactivate enzyme added to the dry analytical element are preferable.

Among these anionic surfactants, alkylbenzenesulfonate is preferable, and alkylbenzenesulfonate having an alkyl chain containing 10 to 14 carbon atoms is more preferable. Moreover, straight-chain dodecylbenzenesulfonate containing 12 carbon atoms, which is a main component of detergent, is further preferable. As salts, sodium salts are preferable. However, potassium salts or lithium salts may also be used. It may also be possible to form salts in the dry analytical element after addition of alkylbenzenesulfonate.

As an anionic surfactant having a carboxy group, bile salts having action to activate lipase are preferable. Preferred examples include deoxycholate, cholate, taurocholate, taurodeoxycholate, and deoxytaurocholate. Particularly preferred examples include sodium deoxycholate and sodium taurodeoxycholate.

The optimal combination of anionic surfactants is sodium deoxycholate, sodium taurodeoxycholate, and straight-chain dodecylbenzenesulfonate.

The additive amount of alkylphenylsulfonate in the present invention is not particularly limited, as long as the effect of the present invention can be achieved. The additive amount of alkylphenylsulfonate is preferably 0.1 to 10 $g/m^2$, more preferably 0.2 to 5 $g/m^2$, and further preferably 0.5 to 5 $g/m^2$.

The reagent layer or spreading layer of the analytical element of the present invention may also comprise surfactants other than the aforementioned anionic surfactant, such as a nonionic surfactant. A surfactant used contains a combination of a lipophilic group such as an alkyl group, an alkylphenyl group, a styrenated phenyl group, a benzilphenyl group or a sorbitanalkyl group, with a hydrophilic group such as a polyoxyethylene group, a polyglycerol group or a polyoxyethylenepolypropylene polymer. Examples of such surfactant include polyoxyethylene alkylether, polyoxyethylene branched alkylether, polyoxyalkylene alkylether, polyoxyethylene alkylphenylether, and alkylphenyl polyglyceride. Specific examples thereof include polyoxyethylene tridecylether, polyoxyethylene branched decylether, polyoxyethylene p-octylphenyl ether, polyoxyethylene p-nonylphenyl ether, polyoxyethylene oleyl ether, polyoxyethylene sorbitan monolaurate, p-nonylphenoxypolyglycidol, and octylglucoside. Among such nonionic surfactants, polyoxyethylene tridecylether, polyoxyethylene branched decylether, p-octylphenoxypolyethoxyethanol, p-nonylphenoxypolyethoxyethanol, p-nonylphenoxypolyglycidol, and the like are preferable. By adding a nonionic surfactant in a spreading layer, a function of developing an aqueous liquid sample (metering function) is further improved. By adding a nonionic surfactant in a reaction layer, water contained in an aqueous liquid sample is facilitated to be absorbed to a reaction layer in a substantially uniform manner upon analysis operations. Also in such case, the liquid comes into contact with a spreading layer in a rapid and substantially uniform manner.

A preferred method for producing the dry analytical element of the present invention will be described. A binder such as gelatin and a surfactant are added to a support. A water-soluble coating solution having improved film-forming properties is coated thereto and dried, and thus a reagent layer is prepared. To the reagent layer, peroxidase and leuco dye used as coloring reagents, and as necessary, ATP, magnesium chloride, and a pH buffer may be added. In addition, when gelatin is used as a binder, a so-called hardening agent may be added in order to crosslink the gelatin. With regard to a spreading layer, when fabric or a formed porous membrane is used as a spreading layer, for example, water is added to a reagent layer such that a part thereof is solubilized. Thereafter, a binder is further softened by heating, as necessary, and it is then fixed by applying pressure to a spreading layer membrane and a reagent layer on the support, followed by drying.

(Method for Preparing Triglyceride Solution)

Triglyceride is dissolved in an ethanol solution of a hydrophobic polymer, and it is then added to a dry analytical element. In order to increase coating stability, a surfactant may be added to optimize dynamic/static surface tension. As such a surfactant, a nonionic surfactant is often used. An anionic surfactant may also be used, when it has only little effect on coupled enzyme to be added.

Moreover, it is also possible to prepare a water-system emulsification dispersion solution containing triglyceride and to add it to the dry analytical element. When such an emulsification dispersion solution is prepared, a surfactant or a protective polymer may be added to the solution.

(Coating/Drying Methods)

Among methods of adding reagents such as triglyceride, there is a highly efficient production method comprising a step of using a Giesser device for uniform coating and drying. In such step, drying is preferably hot-air drying. Drying air is at a temperature of preferably 20° C. to 60° C. and particularly preferably 25° C. to 40° C. Preferably, a dew point is 0° C. to 10° C. Preferably, an air flow is 0.5 to 10 m/second. A required time period for drying is a time period during which a solvent is substantially dried. Meanwhile, drying for a long period of time may result in deactivation of a conjugated enzyme, and thus the time period for drying is preferably 1 to 60 minutes. It is also possible to predetermine preferable drying conditions by setting the temperature, dew point, air speed, and direction of drying air and a time period for drying in each of a plurality of drying zones.

Other reagents necessary for the measurement of lipase activity are preferably prepared, separately from preparation of an additive solution of triglyceride. An anionic surfactant acting as a lipase activator, such as deoxycholate or taurodeoxycholate, colipase, coupled enzyme monoglyceride lipase, and a pH buffer are dissolved in distilled water. In order to improve coating compatibility and blood-developing ability, a binder and a surfactant may be added. $CaCl_2$ may be added to any coating solution. However, it may react with deoxycholic acid so as to form an aggregate in some cases. Thus, it is preferable to dissolve $CaCl_2$ in a substrate solution for addition. The pH is preferably adjusted to pH 7 to 9, which is close to the optimal pH of pancreatic lipase. Basically, each reaction reagent may be added to any layer upon production, provided that reagent conditions appropriate for reaction can be determined upon reaction of lipase in a specimen via dissolution and dispersion. The reaction reagent solution may also be added to the spreading layer by the aforementioned coating/drying methods.

Regarding a method for adding a reagent, impregnation or spraying may be carried out, as long as a uniform amount of a reagent can be determined. Regarding the order of preparation of individual layers, a method whereby a uniform layer in which a reagent is not degraded is obtained may be used.

In view of production, packaging, transportation, storage, measurement operations, and other points, it is preferable to use the integrated multilayer analytical element of the present invention in a manner such that it is cut into square pieces having sides each approximately 10 mm to 30 mm in length or circular pieces having sizes similar to the sizes of the square pieces, following which the pieces are accommodated in slide frames or the like disclosed in the following documents so as to be used as analytical slides: JP Patent Publication (Kokai) No. 57-63452 A (1982); JP Patent Publication (Kokai) No. 54-156079 A (1979); JP Utility Model Publication (Kokai)

No. 56-142454 U (1981); JP Utility Model Publication (Kokai) No. 58-32350 U (1983); and JP Patent Publication (Kokai) No. 58-501144 A (1983).

The integrated multilayer analytical element of the present invention is used as follows. An aqueous liquid sample in an amount of approximately 5 µl to 30 µl, and preferably approximately 8 µl to 15 µl, is supplied by spotting to a porous spreading layer according to the methods according to the above documents. If necessary, incubation is carried out at a substantially constant temperature in the range of approximately 20° C. to 45° C. Then, reflective photometry is carried out from the light-permeable support side of the integrated multilayer analytical element in order to observe detectable changes therein, including color change and coloring. Thereafter, the target components to be measured in a liquid sample are analyzed based on the principles of calorimetric methods.

In the present invention, the body fluids of a dog, a cat, or other animals may be used. Otherwise, a human body fluid may also be used.

The present invention is hereafter described in greater detail with reference to the following examples, although the technical scope of the present invention is not limited thereto.

EXAMPLES

Comparative Example 1-1

Preparation of Slide used in Pancreatic Lipase Analysis (1) Preparation of Glycerin Coloring Reagent:

A reagent with the following composition was coated as an aqueous solution at a density of 127 g/m² to a gelatin-undercoated polyethylene terephthalate film with a thickness of 180 µm, which was smooth, colorless and transparent, followed by drying. Subsequently, water was uniformly supplied to the film such that the film became wet. Tricot knitted fabric prepared by knitting (36 gauge) with polyethylene terephthalate spun yarn corresponding to 50 deniers was laminated thereon via light pressurization. The gelatin was solidified at a drying temperature of 20° C., followed by drying at 45° C. In addition, the coating solution containing a pH buffer PIPES used was adjusted to have a pH of 5.5 with 1 N—NaOH aqueous solution.
Gelatin: 12 g/m²
PIPES (Dojindo Laboratories): 1.5 g/m²
Magnesium chloride (Wako Pure Chemical Industries, Ltd.): 0.52 g/m²
ATP-2 sodium chloride (Oriental Yeast Co., Ltd.): 1.4 g/m²
Polyoxyethylene tridecylether HLB14.8 (Dai-ichi Kogyo Seiyaku Co., Ltd.): 0.3 g/m²
Polyethylene alkyl branched decylether HLB15.9 (Dai-ichi Kogyo Seiyaku Co., Ltd.): 0.06 g/m²
Leuco dye: 0.21 g/m²
Horseradish peroxidase (TOYOBO Co., Ltd): 14 KU/m²
Glycerol kinase (Asahi Kasei Corporation): 3.8 KU/m²
L-α-glycerophosphate oxidase (Asahi Kasei Corporation): 19 KU/m²
1,2-bis(vinylsulfonylacetamide)ethane: 0.12 g/m²

(2) Addition of Substrate and Lipase Reaction Supporting Agents (Formation of Reaction Layer):

Triolein was dissolved in an ethanol solution of polyvinylpyrrolidone used as a hydrophilic polymer. The obtained solution was coated at a density of 220 g/m² onto the aforementioned fabric, and it was then subjected to hot-air drying at a drying temperature 32° C. by a wind with a dew point of 0° C. Thereafter, other reagents for lipase reaction were dissolved in water. The obtained solution was then coated at a density of 145 g/m² to the aforementioned fabric, and it was then dried, so as to produce a pancreatic lipase dry analytical element. A coating solution containing a pH buffer HEPES was adjusted to have a pH of 8.0 with 1 N NaOH aqueous solution, and it was used. The dry amount of coating is as described below.
Calcium chloride (Wako Pure Chemical Industries, Ltd.) 0.18 g/m²
Triolein (95%, MP-Biomedicals) 3.3 g/m²
HEPES (Dojindo Laboratories) 6.1 g/m²
Straight-chain sodium dodecylbenzenesulfonate (Wako Pure Chemical Industries, Ltd.) 1.0 g/m²
Sodium deoxycholate (Wako Pure Chemical Industries, Ltd.) 4.6 g/m²
Sodium taurodeoxycholate 1.5 g/m²
Monoglyceride lipase (Asahi Kasei Corporation) 4400 U/m²
Pig colipase (Roche) 0.1 g/m²
Ascorbate oxidase (TOYOBO Co., Ltd) 8500 U/m²
Polyvinylpyrrolidone (PVP) K90 2.4 g/m²

Comparative Example 1-2

An experiment was carried out in the same manner as that described in Comparative example 1-1 with the exception that triolein (95%, MP-Biomedicals) was used in an amount of 2.2 g/m².

Examples 1-1 to 1-7

Each experiment was carried out in the same manner as that described in Comparative example 1 with the exception that the amount of triolein and the amount of a hydrophilic polymer PVPK90 were determined as those described in Table 1 below, so as to produce various types of pancreatic lipase analytical slides. The conditions are as shown in Table 1.
Measurement 1
(1) Transcription of Triolein from Fabric Surface of Lipase Analytical Element onto Fabric Surface of Fuji Dry Chem Triglyceride Slide:

A 4×3 cm portion of the coating surface of the product of each example was rubbed with a triglyceride slide of Fuji Dry Chem for transcription, and it was remounted using a manual processor. Thereafter, a 7% human albumin normal saline solution was dotted thereto using an FDC5500 analyzer, and the color development OD of each triglyceride slide was then measured. A difference (ΔOD) between the OD of each slide and the OD of a control (a slide that rubbed the ground surface of Comparative example 1, to which no triolein had been coated) was used as an indicator of triolein transcription. Conditions for the comparative examples and examples and the results of triolein transcription are shown in the following Table 1.

TABLE 1

| Experiment No. | | Polymer amount (g/m²) | Triolein amount (g/m²) | Polymer/triolein ratio | Triolein transcription amount (ΔOD) |
|---|---|---|---|---|---|
| Comparative | 1-1 | 2.4 | 3.3 | 0.74 | 0.51 |
| Examples | 1-2 | 2.4 | 2.2 | 1.1 | 0.47 |
| Examples | 1-1 | 2.4 | 1.1 | 2.2 | 0.24 |
| | 1-2 | 10.5 | 3.3 | 3.2 | 0.27 |
| | 1-3 | 10.5 | 2.2 | 4.8 | 0.17 |
| | 1-4 | 10.5 | 1.1 | 9.6 | 0.10 |
| | 1-5 | 20.6 | 3.3 | 6.2 | 0.10 |
| | 1-6 | 20.6 | 2.2 | 9.4 | 0.069 |
| | 1-7 | 20.6 | 1.1 | 19 | 0.031 |

The results are shown in FIG. 1. The error bar is a standard deviation (N=3).

The results show the following. When the ratio of the coating amount of triolein to the coating amount of a hydrophilic polymer is high, the amount of triolein transcribed is increased. If the amount of the hydrophilic polymer is larger than the amount of triolein, transcription can be suppressed.

Next, the amount of triolein transcribed was measured at the stage of winding the coated analytical element in a step of adding the triolein.

Comparative Examples 2-1 and 2-2, and Examples 2-1 to 2-5

In Comparative example 1, after a glycerin coloring reagent had been produced, triolein, hydrophilic polymer and each reagent were dissolved in ethanol, and the obtained solution was then coated onto a fabric, resulting in the coating amounts as shown in Table 2. Thereafter, it was subjected to hot-air drying at a drying temperature 32° C. by a wind with a dew point of 0° C., followed by winding it. The additive amounts of each triolein and each hydrophilic polymer and their ratio applied in the triolein addition step are as shown in Table 2. The amount of triolein transcribed was measured by the method described in Measurement 1. The results are shown in Table 2 below.

TABLE 2

| Examples | Type of hydrophilic polymer | Hydrophilic polymer amount (g/m²) | Triolein (g/m²) | Weight ratio of water-soluble polymer/triolein | Triolein transcription amount (ΔOD) |
|---|---|---|---|---|---|
| Comparative example 2-1 | PVPK90 | 2 | 3.3 | 0.61 | 0.511 |
| Comparative example 2-2 | PVPK90 | 2 | 2.2 | 0.91 | 0.474 |
| Example 2-1 | PVPK90 | 2 | 1.1 | 1.8 | 0.163 |
| Example 2-2 | PVPK17 | 10 | 1.1 | 9 | 0.070 |
| Example 2-3 | PVPK17 | 20 | 1.1 | 18 | 0.067 |
| Example 2-4 | PVPK17 | 30 | 1.1 | 27 | 0.055 |
| Example 2-5 | PVPK17 (10) + PVP90 (2) | 12 | 1.1 | 11 | 0.085 |

Examples 3-1 to 3-4

The production process up to addition of triolein was carried out by the same method as that described in Example 2, and the amount of triolein transcribed was measured by the method described in Measurement 1. The results are shown in Table 3 below. When the weight ratio of a water-soluble polymer/triolein was high, the amount of triolein transcribed was suppressed. The use of hydroxypropylcellulose was also effective.

TABLE 3

| Examples | Type of hydrophilic polymer | Hydrophilic polymer amount (g/m$^2$) | Triolein (g/m$^2$) | Weight ratio of water-soluble polymer/triolein | Triolein transcription amount (ΔOD) |
|---|---|---|---|---|---|
| 3-1 | PVPK90 | 10 | 1.1 | 9.1 | 0.093 |
| 3-2 | PVPK90 | 20 | 1.1 | 19 | 0.051 |
| 3-3 | Hydroxypropylcellulose | 10 | 1.1 | 9.1 | 0.184 |
| 3-4 | Hydroxypropylcellulose | 20 | 1.1 | 19 | 0.112 |

Measurement 2

(1) Transcription of Triolein in Intermediate Product of Lipase Analytical Element from Fabric onto Support The fabric side of each of the reagent-coated products with a size of 10 cm×12 cm of Examples 2-1 to 2-5 (3 sheets for each standard) was laminated on a support (PET base) with a size of 18 cm×10 cm. On each of such 15 products (5 standards×3 sheets) formed by laminating the coated products on the supports, a stainless-steel plate with a size of 10 cm×10 cm was placed. Thereafter, a load of 3280 g was imposed thereon to give a uniform pressure thereto. The product was left in this state at 25° C. for 2 full days. A 10 cm×10 cm portion of the support, on which triolein had been transcribed due to its contact with the fabric surface of the reagent-coated product (on which triolein had been attached), was rubbed with the fabric surface of a Fuji Dry Chem triglyceride slide, so that the triolein attached to the support was transcribed on the triglyceride slide. To this triglyceride slide, a 7% human albumin normal saline solution was dotted using an FDC7000 analyzer, and the color development amount that depended on the transcribed triolein was measured.

TABLE 4

| Examples | Type of hydrophilic polymer | Weight ratio of hydrophilic polymer/triolein | Amount of triolein transcribed on support (ΔOD) |
|---|---|---|---|
| Example 2-1 | PVPK90 | 1.8 | 0.0094 |
| Example 2-2 | PVPK17 | 9 | 0.0072 |
| Example 2-3 | PVPK17 | 18 | 0.0005 |
| Example 2-4 | PVPK17 | 27 | 0 |
| Example 2-5 | PVPK17 (10) + PVP90 (2) | 11 | 0.0009 |

From the results as shown in Table 4, it is found that as the additive amount of a water-soluble polymer is increased with respect to triolein, transcription of the triolein is decreased.

Measurement 3: Slip Failure at Stage of Transportation in Lipase Dry Analytical Element Production Process The production intermediate products of Comparative example 2-2 and Example 3-3, regarding which the step of adding triolein had been completed, were transported at a rate of 30 m/min in the direction of attaching the support side to a transportation roll (made of stainless steel), so that a transportation test was carried out. The results are shown in Table 5.

TABLE 5

| | Slip length at transportation of 150 m |
|---|---|
| Comparative example 2-1 | Untransportable |
| Example 2-1 | 40 m |
| Example 3-3 | 12.3 m |

In such transportation at a rate of 30 m/min under the conditions as described in the above example, as the additive amount of a water-soluble polymer was increased with respect to triolein, the length of a slip was decreased. In the case of transportation at a rate of 10 m/min, no slip was generated.

Measurement 4: Reduction of Friction Due to Transcription of Lipase Dry Analytical Element Triolein onto Support After completion of the transportation test in the production process of each of Examples 2-1 and 3-3 in Measurement 3, a new support was set in a suction drum (which is a roll for base transportation that transports while aspirating the base). The maximum friction was determined when the base was slipped out of the suction drum by horizontally pulling it while aspirating the base.

TABLE 6

| | Maximum static friction (kg weight) |
|---|---|
| Control (Non-contaminated support) | 12 |
| Example 2-1 | 7.5 |
| Example 3-3 | 10.3 |

It is found that, as the additive amount of a water-soluble polymer is increased with respect to triolein, a decrease in the friction of the base transportation roll can be suppressed.

Example 4

Production of Pancreatic Lipase Analytical Slide to which Triolein is Added as Emulsification Dispersion Solution (1) Production of Triolein Microemulsification Dispersion Solution 4.0 g of polyvinylpyrrolidone K90 (manufactured by BASF), 6.0 g of gelatin (manufactured by Nitta Gelatin Inc.), and 0.5 g of sodium straight-chain dodecylbenzenesulfonate (manufactured by Wako Pure Chemical Industries, Ltd.) were dissolved in 175 ml of purified water at 60° C. for 30 minutes. Thereafter, the temperature of the obtained solution was decreased to 40° C., and 5.0 g of triolein (95%, MP Biomedicals) was added to the aqueous solution while string. The thus obtained, oil-water mixed, roughly dispersed solution was dispersed with an ultrasonic homogenizer US-600T (manufactured by Nippon Seiki Co., Ltd.) for 3 minutes. The resultant was treated 5 times with a stir burst mini ultrahigh-pressure homogenizer (manufactured by Sugino Machine Ltd.) at a pressure of 245 MPa, so as to obtain a microemulsification product.

The volume mean particle size of triolein contained in the obtained emulsification product was measured by Nano Truck UPA (manufactured by Nikkiso Co., Ltd.), which was a dynamic light scattering particle size measurement device. As a result, it was found to be 190 nm.

(2) Addition of Triolein Emulsification Dispersion Product that Contains Hydrophilic Polymer The triolein emulsification dispersion solution produced in Example 4(1) above used as a substrate, a hydrophilic polymer, and calcium chloride were added to the glycerin coloring base (a fabric-laminated product) produced in Comparative example 1-1. A water system was coated in each dry additive amount as described below to the product, so as to product a production intermediate product of dry analytical element. The coating amount was set at 134 g/m$^2$, and other conditions were set at the same as those described in the comparative example.

| | |
|---|---|
| Polyvinylpyrrolidone K90 (BASF) | 1.96 g/m$^2$ |
| Calcium chloride (anhydrous) (Wako Pure Chemical Industries, Ltd.) | 0.18 g/m$^2$ |

The triolein emulsification dispersion solution of Example 4 (the coating amount of each component is as described below)

| | |
|---|---|
| Polyvinylpyrrolidone K90 (BASF) | 0.9 g/m$^2$ |
| 750 gelatin (Nitta Gelatin Inc.) | 1.3 g/m$^2$ |
| Triolein (95%, MP Biomedicals) | 1.1 g/m$^2$ |
| Sodium straight-chain dodecylbenzenesulfonate (Wako Pure Chemical) | 0.11 g/m$^2$ |

The weight ratio of a hydrophilic polymer/triolein in the triolein emulsification dispersion solution was 4.

(3) Addition of Lipase Reaction Supporting Agents:

Thereafter, the following reagents were dissolved in water. The obtained solution was coated at a density of 145 g/m$^2$, and it was then dried, so as to produce a pancreatic lipase dry analytical element. The coating solution containing a pH buffer HEPES was adjusted to have a pH of 8.0 with a 1 N—NaOH aqueous solution, and it was then used.

HEPES (Dojindo Laboratories) 6.1 g/m$^2$
Sodium straight-chain dodecylbenzenesulfonate (Wako Pure Chemical Industries, Ltd) 1.0 g/m$^2$
Sodium deoxycholate (Wako Pure Chemical Industries, Ltd.) 4.6 g/m$^2$
Sodium taurodeoxycholate 1.5 g/m$^2$
Metolose 2.1 g/m$^2$
Monoglyceride lipase (Asahi Kasei Corporation) 4400 U/m$^2$
Pig colipase (Roche) 0.1 g/m$^2$
Ascorbate oxidase (TOYOBO Co., Ltd) 8500 U/m$^2$ (4) Slip Measurement at Stage of Transportation in Lipase Dry Analytical Element Production Process The production intermediate product of Example 4(2), regarding which the step of adding triolein had been completed, was subjected to an experiment regarding slip failure by the method described in Measurement 2. The product was transported at a rate of 30 m/min in the direction of attaching the support side to a transportation roll (made of stainless steel). As a result, in the case of the production intermediate product of Example 3, a slip generated at a transportation of 150 m was found to be 13 m. Thus, it was found that the slip was reduced when compared with the result of Comparative example 2-1. In addition, the product was transported at a rate of 10 m/min. As a result, no slip was generated.

The invention claimed is:

1. A dry analytical element for measuring pancreatic lipase contained in body fluid, which comprises triglyceride of long chain alkyl fatty acid having 12 to 22 carbon atoms, monoglyceride lipase, and a glycerin measurement reagent, and which comprises a water-impermeable support and at least one spreading or reagent layer, wherein a hydrophilic polymer at a weight ratio of 1.8:1 or greater with respect to the triglyceride is contained.

2. The dry analytical element according to claim 1, wherein a hydrophilic polymer at a weight ratio of 5:1 or greater with respect to the triglyceride is contained.

3. The dry analytical element according to claim 1, which a hydrophilic polymer at a weight ratio of 10:1 or greater with respect to the triglyceride is contained.

4. The dry analytical element according to claim 1, wherein the hydrophilic polymer is selected from among polyvinylpyrrolidone, polyacrylamide, a cellulose derivative, gelatin, and a combination thereof.

5. The dry analytical element according to claim 4, wherein the cellulose derivative is hydroxypropylcellulose, hydroxyethylcellulose, or methylcellulose.

6. The dry analytical element according to claim 1, wherein the glycerin measurement reagent comprises glycerin kinase, glycerophosphate kinase, peroxidase, and a coloring reagent.

7. The dry analytical element according to claim 1, wherein the monoglyceride lipase is derived from *Bacillus stearothermophilus* H-165.

8. The dry analytical element according to claim 1, wherein the triglyceride is triolein.

9. The dry analytical element according to claim 1, wherein the dry analytical element for measuring pancreatic lipase contained in body fluid has a structure comprising a water-impermeable support, a reagent layer, and a spreading layer.

10. The dry analytical element according to claim 1, wherein the spreading layer consists of a fabric or a porous membrane.

11. The dry analytical element according to claim 10, wherein the porous membrane is a porous membrane of acetylcellulose or polysulfone, or a porous membrane formed from microbeads.

12. A method for producing a dry analytical element for measuring pancreatic lipase contained in body fluid, which comprises triglyceride of long chain alkyl fatty acid having 12 to 22 carbon atoms, monoglyceride lipase, and a glycerin measurement reagent, and which comprises a water-impermeable support and at least one spreading or reagent layer, which comprises a step of coating the triglyceride in a state where the dry analytical element comprises a hydrophilic polymer at a weight ratio of 1.8:1 or greater with respect to the triglyceride.

13. The method according to claim 12, which comprises coating the triglyceride in a state where the dry analytical element comprises a hydrophilic polymer at a weight ratio of 5:1 or greater with respect to the triglyceride.

14. The method according to claim 12, which comprises coating the triglyceride to the dry analytical element in a state where the dry analytical element comprises a hydrophilic polymer at a weight ratio of 10:1 or greater with respect to the triglyceride.

15. The method according to claim 12, wherein the hydrophilic polymer is selected from among polyvinylpyrrolidone, polyacrylamide, a cellulose derivative, gelatin, and a combination thereof.

16. The method according to claim 15, wherein the cellulose derivative is hydroxypropylcellulose, hydroxyethylcellulose, or methylcellulose.

17. The method according to claim 12, wherein the triglyceride is triolein.

* * * * *